(12) United States Patent  
Gournay et al.

(10) Patent No.: US 6,709,434 B1  
(45) Date of Patent: Mar. 23, 2004

(54) SPINAL OSTEOSYNTHESIS DEVICE

(75) Inventors: Jose Gournay, Dammartin en Goele (FR); Serge Governatori, Nice (FR)

(73) Assignee: Sofamor S.N.C., Roissy CDG Cedex (FR)

( * ) Notice: Subject to any disclaimer, the term of this patent is extended or adjusted under 35 U.S.C. 154(b) by 0 days.

(21) Appl. No.: 09/744,407

(22) PCT Filed: Jul. 29, 1999

(86) PCT No.: PCT/IB99/01355

§ 371 (c)(1),  
(2), (4) Date: May 16, 2001

(87) PCT Pub. No.: WO00/06038

PCT Pub. Date: Feb. 10, 2000

(30) Foreign Application Priority Data

Jul. 30, 1998 (FR) .............................................. 98 09791

(51) Int. Cl.[7] .............................................. A61B 17/56
(52) U.S. Cl. .............................. 606/61; 606/60; 606/72; 606/73
(58) Field of Search .............................. 606/61, 72, 73, 606/60; 285/112; 403/2; 411/81

(56) References Cited

U.S. PATENT DOCUMENTS

| 5,312,404 | A | * | 5/1994 | Asher et al. .................. 606/61 |
| 5,474,551 | A |   | 12/1995 | Finn et al. |
| 5,486,174 | A |   | 1/1996 | Fournet-Fayard et al. |
| 5,487,744 | A | * | 1/1996 | Howland ...................... 606/61 |
| 5,545,167 | A | * | 8/1996 | Lin ............................. 411/349 |
| 5,562,661 | A | * | 10/1996 | Yoshimi et al. ................ 606/59 |
| 5,697,929 | A | * | 12/1997 | Mellinger ...................... 411/5 |
| 5,725,528 | A |   | 3/1998 | Errico et al. |
| 5,735,851 | A |   | 4/1998 | Errico et al. |
| 5,876,403 | A | * | 3/1999 | Shitoto ........................ 606/53 |
| 5,879,351 | A | * | 3/1999 | Viart ........................... 606/61 |
| 5,957,425 | A | * | 9/1999 | Conway et al. ............. 248/548 |
| 6,170,884 | B1 | * | 1/2001 | McLennan et al. .......... 285/112 |
| 6,179,838 | B1 | * | 1/2001 | Fiz ............................... 606/61 |
| 6,187,005 | B1 | * | 2/2001 | Brace et al. .................. 606/61 |
| 6,280,445 | B1 | * | 8/2001 | Morrison et al. ............. 606/61 |
| 6,416,515 | B1 | * | 7/2002 | Wagner ....................... 606/61 |

FOREIGN PATENT DOCUMENTS

| EP | 0 729 731 A1 | 4/1996 |
| FR | 2 692 471 A1 | 12/1993 |
| WO | WO 98/15233 | 4/1998 |

* cited by examiner

*Primary Examiner*—Henry Bennett  
*Assistant Examiner*—Azy Kokabi  
(74) *Attorney, Agent, or Firm*—Woodard, Emhardt, Moriarty, McNett & Henry LLP

(57) ABSTRACT

A spinal osteosynthesis device comprising a bone anchorage element, a vertebral rod, a connector for interconnecting the rod and the anchorage element so that the anchorage element is capable of being angularly oriented in a polyaxial manner relative to the rod. A fixation element is provided for fixing the position of the connector in translation and in rotation relative to the rod. A clamp element is provided for clamping the bone anchorage element to the connector in a predetermined angular position independent of the fixation element.

35 Claims, 1 Drawing Sheet

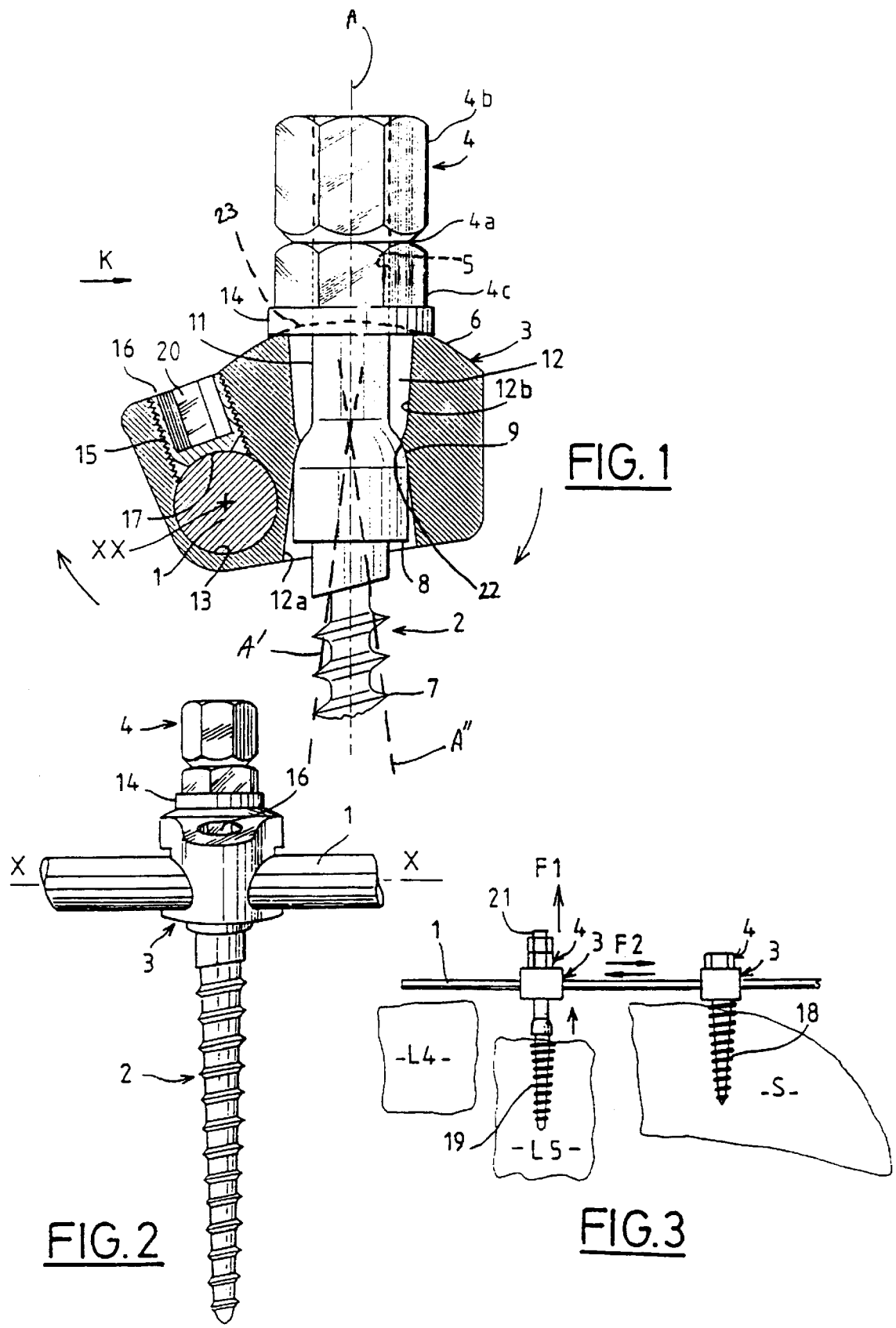

SPINAL OSTEOSYNTHESIS DEVICE

TECHNICAL FIELD BACKGROUND

The present invention relates to a bone implant apparatus, and more specifically but not exclusively a spinal osteosynthesis device of the type including a bone anchorage element, a vertebral rod, and a connector for interconnecting the rod and the anchorage element such that the anchorage element is capable of being angularly oriented in a polyaxial manner relative to the rod.

BACKGROUND

U.S. Pat. No. 5,486,174 and EP-A-0612507 describe such devices in which the connector is constituted by two jaws which define a lateral recess for the rod and in which conical openings are provided for the passage of the bone anchorage element. The latter comprises a shank having a double screw thread, one end part of which constitutes a bone anchorage screw. The opposite threaded end part projects from the upper jaw to permit the clamping of the assembly of the parts by a nut which comes to bear against the upper jaw.

Provided between the two threaded parts of the anchorage element shank is a spherical shoulder which comes to bear against the conical wall of the opening of the connector.

In this device, as in other known spinal osteosynthesis systems, a single nut is used to clamp the anchorage element, the connector and the rod in a chosen position. Consequently, if it is desired to increase the spacing between two consecutive anchorage elements, for example in the treatment of spondylolisthesis or for restoring a discal height or recreating a lordosis it is in fact only possible to slightly incline the anchorage element, without obtaining the desired increase in the spacing.

SUMMARY OF INVENTION

One object of the invention is to provide a spinal osteosynthesis device so arranged as to easily permit such an adjustment of the spacing between two successive anchorage elements.

One form of the present invention is a unique bone implant device. A further form is a unique spinal implant apparatus. Still a further form is a unique spinal osteosynthesis method.

According to another form of the invention, the spinal osteosynthesis device comprises separate means, on one hand means for fixing the position of the connector in translation and in rotation on the rod and, on the other hand, means for independently clamping the bone anchorage element to the connector in the chosen angular position. Such a separation of the clamping means permits easily adjusting the position of the connector, and consequently of the bone anchorage element, in translation on the rod, relative to the neighboring bone anchorage element and therefore obtaining an improved correction.

Further objects, forms, embodiments, aspects, features, benefits and advantages of the present invention will be apparent to one of ordinary skill in the art from the following description and drawings.

BRIEF DESCRIPTION OF DRAWINGS

The invention will now be described with the reference to the accompanying drawings which illustrate an embodiment thereof by way of a non-limitative example.

FIG. 1 is a partial half cross-sectional view, half elevational view to an enlarged scale of an embodiment of the spinal osteosynthesis device according to the invention.

FIG. 2 is an elevational view to a smaller scale, in the direction of arrow K, of the device of FIG. 1.

FIG. 3 is a diagrammatic elevational view illustrating the application of the device of FIGS. 1 and 2 to the treatment of spondylolisthesis.

DESCRIPTION OF PREFERRED EMBODIMENT

The spinal osteosynthesis device illustrated in FIGS. 1 and 2 comprises a vertebral rod 1, a bone anchorage element 2 constituted in this embodiment by a pedicle screw, and a connector 3 for interconnecting rod 1 and anchorage element 2. This embodiment includes a nut 4 for clamping the assembly of the parts 1, 2, and 3, which is adapted to be screwed on a threaded end part 5 of bone anchorage element 2.

Bone anchorage part 7 is in the illustrated embodiment a screw which is extended by a cylindrical head 8 itself followed by a convex and preferably spherical bearing surface 9 which has the same center of curvature as surface 6 and is connected to end part 5 by a smooth shank 11.

Head 8, bearing surface 9 and shank 11 are disposed in an opening 12 extending throughout connector 3 in a direction substantially perpendicular to the longitudinal axis XX of the rod 1. Rod 1 is itself disposed in a cylindrical channel 13 formed in connector 3 to one side of opening 12. Opening 12 has a first conical part 12a which receives head 8 and bearing surface 9, and a second conical part 12b through which extends shank 11 and at the end of which a washer 14 fixed to the nut 4 bears against the bearing surface 6 when the nut 4 is screwed on the threaded end part 5.

Shank 11 is spaced from wall 12b, and walls 12a, 12b and shank 11 are shaped and have a size for allowing a polyaxial orientation of the anchorage element 2.

The connector 3 includes a body portion or a first member that is integral in the illustrated embodiment, i.e. made in one piece, and there is provided transversely of the channel 13 a tapped hole 15 which opens onto channel 13 and in which a screw or a second member 16 is engageable. Screw 16 has a bearing surface 17 to enable screw 16 to be screwed down and applied against rod 1 at the end of the screwing. A recess 20 provided in screw 16 is so shaped as to receive a corresponding screwing tool.

The combination of the walls 12a, 12b and the bearing surface 9 which is applied against the end 22 of wall 12a, renders anchorage element 2 polyorientable in multiple directions within limits defined by walls 12a, 12b. This polyorientability helps the surgeon to achieve a close adaptation of the osteosynthesis device of the present invention to the anatomy of the considered vertebral segment while limiting as far as possible the extent to which rod 1 must be bent. Whatever be the orientation imparted to anchorage element 2, washer 14 fixed to nut 4 bears against bearing surface 6, and to this end washer 14 is provided with a concave internal bearing surface 23.

In one embodiment of the invention, opening 12 has a longitudinal axis A, which may correspond to a longitudinal axis of bone anchorage element 2, as illustrated in FIG. 1. The size and shape of walls 12a, 12b permit bone anchorage element 2 to be selectively oriented at any of a number of angles in three dimensions with respect to axis A. For example, bone anchorage element 2 can be placed so that its longitudinal axis substantially coincides with one of axes A' or A″, or at any position within the cone formed by rotation of axis A′ and/or A″ about axis A. Bone anchorage element 2 therefore enjoys at least two degrees of freedom in its orientability. Walls 12a, 12b of connector 3 could be configured to allow bone anchorage element 2 to be positioned at any angle between about 0 and 45 degrees with respect to axis A. In the specific embodiment shown in FIG. 1, bone anchorage element 2 can be oriented at any angle between about 0 and 8 degrees with respect to axis A.

The present invention therefore permits separating the operations of adjusting, on one hand, the position in translation and rotation of connector 3 on rod 1, and, on the other hand, the clamping of the angular position of connector 3 on anchorage element 2, thereby enabling the surgeon to effect these two adjustments separately.

In the case, for example, of an application of the apparatus of the present invention to the correction of a spondylolisthesis (FIG. 3), a first bone anchorage element 18 is anchored in the sacrum S and a second bone anchorage element 19 is anchored in the vertebra L5 having the spondylolisthesis to be corrected. Rod 1 extends through the two connectors 3, respectively associated with the anchorage elements 18 and 19 and capable of being clamped in position by respective nuts 4, each connector 3 being provided with a screw 16.

The surgeon uses as a support anchorage element 18, which constitutes a fixed point. He tightens nut 4 on connector 3 associated with anchorage element 19 of the vertebra L5 to be corrected. This tightening has a taking up effect (arrow F1) by the rearward pull on anchorage element 19 toward connector 3 (while rod 1 remains fixed). This displacement, substantially a simple translation along rod 1, may be advantageously completed, owing to the invention, by an adjustment of the position of connector 3 of anchorage element 19, its set screw 16 being unscrewed to permit this adjustment. Thus, the position of the vertebra L5 to be corrected may be adjusted not only in accordance with the above described method by a simple pivoting of its anchorage element 19 about the fixed bearing point on the sacrum S but also by an adjustment (arrow F2) along rod 1, by separate means, namely nut 4 and screw 16 provided by the invention. This permits in this case restoring a discal height or restoring a local lordosis. The threaded part 21 of anchorage element 19 projects from the nut 4, which has a fracture-initiating region 4a defining a part 4b remote from connector 3 and a part 4c close to connector 3.

After nut 4 has been clamped on connector 3, threaded part 21 that projects beyond the upper part 4b of nut 4, together with said upper part 4b, is broken off and removed. Nonetheless, in other embodiments a break-off operation may not be desired. Accordingly the present invention also contemplates a non-frangible nut that does not include a fracture-initiating region. Such a non-frangible nut is threaded onto threaded part 21 of anchorage element 19 into contact with bearing surface 6 of connector 3 in one embodiment and tightened with an appropriate tool.

Thus, one embodiment of the present invention contemplates a bone implant apparatus including a rod, a bone anchorage element with a distal anchoring portion, a proximal threaded shank portion, and a head portion, and a connector that connects the rod and the bone anchorage element. The connector defines an opening that receives the bone anchorage element, a channel adapted to receive the rod and offset from the opening, and a threaded hole in communication with the channel. The opening is bounded by one or more walls with a portion that engages the head of the bone anchorage element and that is shaped and sized to permit multi-axial orientation of the bone anchorage element with respect to the opening. A set screw is threaded into the threaded hole and bears against the rod when the rod is within the channel of the connector, and a nut is provided for threading on the proximal portion of the bone anchorage element to lock the bone anchorage element in a desired orientation.

Another embodiment of the present invention contemplates a connector for connecting a bone anchorage element to a rod in a bone implant apparatus. Connector includes a first member having an opening configured to receive the bone anchorage element, a channel offset from said opening and configured to receive the rod, and an internally threaded hole communicating with the channel. The opening is bounded by at least one wall configured to allow the bone anchorage element to be oriented polyaxially with at least two degrees of freedom. A second member, such as a set screw, is threaded within the internally threaded hole and can be threaded down against the rod to lock the first member with respect to the rod.

Other variations and alternatives in the above-described structures are contemplated to be a part of the present invention. For example, connector 3 can be assembled or fashioned from multiple pieces interlocked or otherwise fastened together. As another example, the connector of the present invention could permit polyaxial positioning of a bone anchorage element while being incapable of translation or rotation with respect to a rod, such as where the connector is permanently fixed to the rod. Such a connector includes an opening identical or similar to opening 12 of connector 3 (FIG. 1). As a further example, the constructs of the present invention can be used on other portions of the spine above the lower lumbar vertebrae, or on other portions of the body, such as the long bones.

The invention is applicable to other corrections such as those mentioned before and various variants thereof may be envisaged.

What is claimed is:

1. A spinal osteosynthesis device, comprising:
    a rod;
    a bone anchor having an anchoring portion and a connection portion;
    a connector defining an opening adapted to receive said connection portion of said bone anchor therein and a channel offset from said opening and adapted to receive a portion of said rod therein, said opening bound by at least one conical wall adapted to engage said connection portion to permit multi-axial orientation of said bone anchor within said opening; and
    a clamp member adapted for engagement with said connector and said bone anchor to lock said bone anchor in a selected orientation within said opening; and
    wherein said multi-axial orientation of said bone anchor within said opening occurs about at least two axes so as to define at least two degrees of freedom.

2. The device of claim 1 wherein said connection portion of said bone anchor includes a head portion and a shank portion, said shank portion extending through said opening in said connector, said head portion engaging said at least one conical wall to permit said multi-axial orientation of said bone anchor within said opening.

3. The device of claim 2 wherein said head portion defines a spherical bearing surface adapted to engage said at least one conical wall.

4. The device of claim 2 wherein said clamp member engages said connector and said shank portion of said bone anchor to lock said bone anchor in said selected orientation.

5. The device of claim 4 wherein said shank portion of said bone anchor is threaded, and wherein said clamp member comprises a nut adapted for threading engagement along said threaded shank portion and into engagement with said connector to lock said bone anchor in said selected orientation.

6. The device of claim 1 wherein said connection portion defines a spherical bearing surface adapted to engage said at least one conical wall to permit said multi-axial orientation of said bone anchor within said opening.

7. The device of claim 1 wherein said connector has a convex surface formed about said opening.

8. The device of claim 7 wherein said convex surface is spherical.

9. The device of claim 7 wherein said clamp member has a concave surface adapted to matingly engage said convex surface of said connector.

10. The device of claim 1 further comprising a fixation member adapted for engagement with said connector and said rod to lock said connector in a fixed position relative to said rod.

11. A bone implant apparatus, comprising:
  a rod;
  a bone anchorage element having a distal anchoring portion, a proximal threaded shank portion, and a head portion between said distal and proximal portions;
  a connector defining an opening therethrough to receive said bone anchorage element, a channel offset from said opening adapted to receive said rod, and a threaded hole in communication with said channel, said opening being bounded by at least one wall having a portion adapted to engage said head portion of said bone anchorage element, said wall being shaped and sized to engage said head portion of said bone anchorage element in a manner to permit multi-axial orientation of said bone anchorage element with respect to said opening;
  a set screw adapted to be threaded into said threaded hole and to bear against said rod when said rod is within said channel; and
  a nut adapted to be threaded on said proximal portion of said bone anchorage element to engage said connector, whereby said bone anchorage element is locked into a variable angular orientation falling within a range of angular orientations relative to said connector.

12. The apparatus of claim 11 wherein said connector is a single piece.

13. The apparatus of claim 11 wherein said connector has an upper convex surface formed around said opening.

14. The apparatus of claim 13 wherein said upper convex surface is spherical.

15. The apparatus of claim 13 wherein said nut has a lower concave surface adapted to matingly engage said upper convex surface of said connector.

16. The apparatus of claim 15 wherein said nut has a first part that includes said lower concave surface, a second part, and a fracture-initiating part between said first and second parts.

17. The apparatus of claim 11, wherein said multi-axial orientation includes selective orientation of said bone anchorage element with at least two degrees of freedom within said opening.

18. A spinal osteosynthesis device, comprising:
  a bone anchorage element;
  a vertebral rod;
  a connector for interconnecting the rod and the anchorage element so that said anchorage element is polyaxially orientable relative to the rod;
  first means for fixing the position of the connector in translation and in rotation on the rod; and
  second means for clamping the bone anchorage element to the connector in a variable angular position falling within a range of angular positions relative to the connector, said second means operating independent of said first means.

19. The device according to claim 18, wherein said bone anchorage element has a threaded end part that projects from the connector, and wherein said independent clamping means comprises a clamping nut adapted to cooperate with said threaded end part; and
  wherein said connector is a single piece and has a spherical bearing surface, and the means for fixing the connector in translation and in rotation on the rod comprises an opening provided in the connector and communicating with a bore which receives the rod and extends throughout the connector, and a rod-clamping element which can be placed in said opening.

20. The device according to claim 19, wherein said opening is tapped and said rod-clamping element is a screw having a bearing surface for bearing against said rod, said opening and said screw being arranged so that said screw is completely insertable in said connector so as to avoid interfering with said nut.

21. The device according to claim 19, wherein said nut comprises a first part close to said connector and a second part remote from said connector between which a fracture-initiating region is provided.

22. The device according to claim 19, wherein said connector has a through aperture bounded by two conical walls, and said anchorage element has a spherical bearing surface adapted to bear on an end portion of one of said conical walls, whereby said anchorage element is polyaxially orientable within said conical walls.

23. A connector for use in connecting a bone anchorage element to a rod in a bone implant apparatus, said connector comprising:
  a first member having an opening configured to receive a portion of the bone anchorage element, a channel offset from said opening and configured to receive a portion of the rod, and a hole communicating with said channel,
  wherein said opening is bounded by at least one wall configured to engage said portion of the bone anchorage element in a manner to allow said portion of the bone anchorage element to be oriented polyaxially with at least two degrees of freedom within said opening, and wherein said hole has an internal thread; and
  a second member threaded within said hole, whereby said second member can be threaded down against said portion of the rod within said channel to lock said first member with respect to the rod; and
  a nut adapted to engage a portion of the bone anchorage element and to lock the first member with respect to the bone anchorage element in a variable angular orientation falling within a range of angular orientations.

24. The connector of claim 23 wherein said connector has an upper convex surface formed around said opening.

25. The connector of claim 24 wherein said upper convex surface is spherical.

26. The connector of claim 24 wherein said nut has a lower concave surface adapted to matingly engage said upper convex surface of said connector.

27. The connector of claim 23 wherein said nut has a first part that includes said lower concave surface, a second part, and a fracture-initiating part between said first and second parts.

28. A bone implant apparatus, comprising:

a rod;

a bone anchorage element having a distal anchoring portion, a proximal threaded shank portion, and a head portion between said distal and proximal portions;

a connector defining an opening therethrough to receive said bone anchorage element, a channel offset from said opening adapted to receive said rod, and a threaded hole in communication with said channel, said opening being bounded by at least one wall having a portion adapted to engage said head portion of said bone anchorage element, said wall of said opening defining a conical portion that is shaped and sized to permit multi-axial orientation of said bone anchorage element with respect to said opening;

a set screw adapted to be threaded into said threaded hole and to bear against said rod when said rod is within said channel; and a nut adapted to be threaded on said proximal portion of said bone anchorage element to engage said connector, whereby said bone anchorage element is locked into a desired orientation.

29. The apparatus of claim 28 wherein said wall of said opening has two conical portions and a concavely rounded surface.

30. The apparatus of claim 29 wherein said concavely rounded surface is spherical.

31. A connector for use in connecting a bone anchorage element to a rod in a bone implant apparatus, said connector comprising:

a first member having an opening configured to receive a portion of the bone anchorage element, a channel offset from said opening and configured to receive a portion of the rod, and a hole communicating with said channel, wherein said opening is bounded by at least one wall, said wall of said opening having two conical portions and a concavely rounded surface, said conical portions being sized to provide for polyaxial rotation of the bone anchorage element with at least two degrees of potential freedom within said opening, and wherein said hole has an internal thread; and a second member threaded within said hole, whereby said second member can be threaded down against said portion of the rod within said channel to lock said first member with respect to the rod.

32. The connector of claim 31 wherein said concavely rounded surface is spherical.

33. A connector for use in connecting a bone anchorage element to a rod in a bone implant apparatus, said connector comprising:

a first member having an opening configured to receive a portion of the bone anchorage element, a channel offset from said opening and configured to receive a portion of the rod, and a hole communicating with said channel, wherein said opening is bounded by at least one wall, said wall of said opening having a conical portion to allow said portion of the bone anchorage element to be oriented polyaxially with at least two degrees of freedom within said opening, and wherein said hole has an internal thread; and a second member threaded within said hole, whereby said second member can be threaded down against said portion of the rod within said channel to lock said first member with respect to the rod.

34. A spinal osteosynthesis device, comprising:

a rod;

a bone anchor having an anchoring portion and a connection portion;

a connector defining an opening adapted to receive said connection portion of said bone anchor therein and a channel offset from said opening and adapted to receive a portion of said rod therein, said opening bound by at least one conical wall adapted to engage said connection portion to permit multi-axial orientation of said bone anchor within said opening;

a fixation member adapted for engagement with said connector and said rod to lock said connector in a fixed position relative to said rod; and a clamp member adapted for engagement with said connector and said bone anchor to lock said bone anchor in a selected orientation within said opening; and wherein said clamp member operates independently of said fixation member.

35. A spinal osteosynthesis device, comprising:

a rod;

a bone anchor having an anchoring portion and a connection portion;

a connector defining an opening adapted to receive said connection portion of said bone anchor therein and a channel offset from said opening and adapted to receive a portion of said rod therein, said opening bound by at least one conical wall adapted to engage said connection portion to permit multi-axial orientation of said bone anchor within said opening;

a fixation member adapted for engagement with said connector and said rod to lock said connector in a fixed position relative to said rod; and a clamp member adapted for engagement with said connector and said bone anchor to lock said bone anchor in a selected orientation within said opening; and wherein said connector defines a threaded hole in communication with said channel; and wherein said fixation member comprises a set screw adapted for threading engagement along said threaded hole and into engagement with said rod.

* * * * *